United States Patent [19]

Yamamoto et al.

[11] Patent Number: 5,380,875

[45] Date of Patent: Jan. 10, 1995

[54] HYDROXYPROLINE DERIVATIVES AND PREPARATIVE PROCESS THEREFOR

[75] Inventors: Yasuo Yamamoto; Yoshiaki Harushima; Akira Nagai, all of Ibaraki, Japan

[73] Assignee: Hitachi Chemical Company, Ltd., Tokyo, Japan

[21] Appl. No.: 224,350

[22] Filed: May 4, 1994

Related U.S. Application Data

[62] Division of Ser. No. 893,994, Jun. 5, 1992.

[30] Foreign Application Priority Data

Jun. 6, 1991 [JP] Japan .................. 3-134908
Jul. 1, 1991 [JP] Japan .................. 3-159309
Jul. 2, 1991 [JP] Japan .................. 3-160741

[51] Int. Cl.$^6$ ................................. C07D 207/12
[52] U.S. Cl. .......................... 548/533; 546/174; 546/208; 546/281; 548/260; 548/519
[58] Field of Search .......................... 548/533

[56] References Cited

U.S. PATENT DOCUMENTS 5,101,059 3/1992 Carpino et al. ............ 549/388

FOREIGN PATENT DOCUMENTS 413277 2/1991 European Pat. Off.

OTHER PUBLICATIONS

Carpino, et al.; J. Org. Chem., (1972), pp. 3404–3409.
Meienhofer, et al.; Peptide Protein Research, (1979), pp. 35–42.
Schon, et al.; Synthesis–Communications, (1986), pp. 303–305.
LaPatsanis, et al.; Synthesis–Communications, (1983), pp. 671–673.
Kisfaludy, et al., Synthesis–Communications (1983), pp. 325–327.

*Primary Examiner*—Joseph P. Brust
*Attorney, Agent, or Firm*—Pennie & Edmonds

[57] ABSTRACT

Provided are N-(9-fluorenylmethoxycarbonyl)-4-substituted proline derivatives represented by the following formula (I):

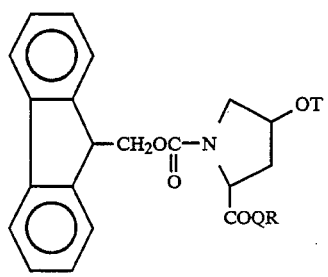

wherein Q is O or S, R represents a particular monovalent group, and T represents H or —C(CH$_3$)$_3$. Where T is H, the derivatives can each be prepared by reacting a corresponding electron attractive compound with N-(9-fluorenylmethoxycarbonyl)-4-hydroxyproline in the presence of a coupling reagent. The derivatives in which T stands for —(CH$_3$)$_3$ can each be prepared by reacting the corresponding N-(9-fluorenylmethoxy-carbonyl)-4-hydroxyproline derivative with isobutylene in the presence of a catalytic amount of sulfuric acid. The staring material, N-(9-fluorenylmethoxycarbonyl)-4-hydroxyproline, can be purified by adsorbing it on anhydrous magnesium sulfate.

2 Claims, 16 Drawing Sheets

HYDROXYPROLINE DERIVATIVES AND PREPARATIVE PROCESS THEREFOR

This is a division of application Ser. No. 07/893,994, filed Jun. 5, 1992.

FIELD OF THE INVENTION

This invention relates to novel 4-hydroxyproline derivatives whose amino group is protected with a 9-fluorenylmethoxycarbonyl (hereinafter abbreviated as "Fmoc") group, novel 4-tert-butyl-hydroxyproline derivatives whose amino group is protected with an Fmoc group, a preparation process thereof, and a purification process of 4-hydroxyproline having an Fmoc-protected amino group and which is useful as one of raw materials for these derivatives.

BACKGROUND OF THE INVENTION

The adhesive protein secreted by shells such as hard-shelled mussel (*Mytilus coruscus*) or acorn barnacle has strong adherent force to a surface of low energy such as a polytetrafluoroethylene surface. One of the amino acids contained in the above mentioned adhesive protein is 4-hydroxyproline.

4-Hydroxyproline is also contained in peptides, such as the peptide of the neurotoxin secreted by the sea snake, which can show physiological effects on the neurons of higher animals. Peptides containing 4-hydroxyproline are, therefore, expected to have utility as a pharmaceutical.

When a peptide is chemically synthesized using an amino acid as a raw material, it first is necessary to use protecting groups to block the functional groups from taking part in a dehydration condensation reaction between the amino and carboxyl groups on the backbone of the amino acid, and the amino, carboxyl and hydroxyl groups on the side chain of the amino acid by protecting groups. The protecting groups then are removed from the intermediates (deprotection) as needed, and allowing the intermediates to take part in the subsequent reaction.

As a method for blocking amino groups on the backbone, protection with benzyloxycarbonyl groups, tert-butyloxycarbonyl groups, Fmoc group or the like is known. Among them, protection with Fmoc groups has been employed because deprotection is feasible under mild basic conditions and chemical synthesis of peptides by a solid-phase technique also is feasible.

Protection of the amino group in amino acids with an Fmoc group and the application of this protection to synthesis of a peptide is disclosed by L. A. Carpino et al. [J. Org. Chem., 37, 3404–3409 (1972)]. Later, J. Meienhofer et al. used it for solid-phase synthesis [Int. J. Peptide Protein Res., 13, 35–42 (1979)].

Techniques such as the symmetric anhydride technique, mixed acid anhydride technique, acid chloride technique, azide technique and active ester technique are known for the dehydration condensation (peptide bonding) of an amino acid whose functional groups (such as amino, carboxyl, and hydroxyl) which do not take part in the dehydration condensation have been protected, and another amino acid whose functional groups (such as amino, carboxyl and hydroxyl) do not take part in the dehydration condensation have been protected. The active ester technique is popular because this technique does not require handling of dangerous reagents such as phosgene. Moreover, the reagents employed in the active ester technique are stable. A variety of reagents for use in the active technique are available on the market.

In the active ester technique, it is known to react electron attractive compounds such as pentafluorophenol or 3-hydroxy-3,4-dihydro- 4-oxobenzo-triazine (hereinafter abbreviated as "Dhbt-OH") represented by formula (IV):

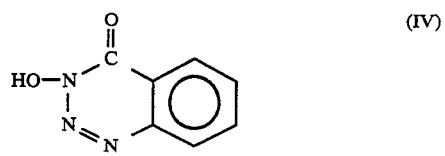

in the presence of a coupling reagent such as dicyclohexylcarbodiimide.

The method of using pentafluorophenol as an electron attractive compound was applied to the solid-phase synthesis of a peptide by L. Kisfaludy et al. [Synthesis, 325 (1983); ibid, 303 (1986)]. According to the Kisfaludy et al. teachings, the pentafluorophenyl ester derivative of an amino acid is obtained by protecting the amino groups on its backbone with tert-buthoxycarbonyl or Fmoc groups and then reacting the amino-protected amino acid with equimolar amounts of pentafluorophenol and dicyclohexylcarbodiimide in a solvent such as dioxane or ethyl acetate.

The method of using Dhbt-OH as an electron attractive compound was developed by W. Koenig et al. [Chem. Ber., 103, 2034–2040 (1970)] and was applied to the solid-phase synthesis of a peptide by E. Atherton et al., L. Cameron et al. and P. Goddard et al. [J. Chem. Soc. Chem. Commn., 1763 (1986); ibid, 270 (1987); ibid, 1025 (1988)]. According to those literature articles, the Dhbt ester derivative of an amino acid is obtained by protecting the amino groups on the backbone of the amino acid with tert-buthoxycarbonyl or Fmoc groups and then reacting the amino-protected amino acid with equimolar amounts of Dhbt-OH and dicyclohexylcarbodiimide in tetrahydrofuran.

In addition to the above, active ester methods in which an amino acid derivative of the free carboxyl type is activated in a reaction system and then subjected to coupling, namely the so-called BOP method [B. Castro et al.: Tetrahedron Letters, 1219 (1975)], TBTU method [R. Knorr et al.: Tetrahedron Letters, 30, 1927–1930 (1989)] and PyBOP method [J. Caste et al.: Tetrahedron Letters, 31, 205–208 (1990)] have been developed. In these methods, an activating reagent is added in the presence of a base to a solution containing an amino acid derivative of the free carboxyl type and HOBt to produce a benzotriazole active ester intermediate, followed by a coupling reaction between the intermediate and an amino acid or peptide to be subjected to an extending reaction. Although these methods are believed to have higher reactivity and to cause less side reactions, they are not employed widely.

In addition to the above mentioned methods, introduction of an Fmoc group to the amino group on the backbone of 4-hydroxyproline is known. L. Lapatsanis et al. [Synthesis, 671–673 (1983)].

It is also known to block the hydroxyl group on the side chain of 4-hydroxyproline, serine or threonine with a protecting group such as a benzyl, substituted benzyl and tert-butyl group [E. Wunsch et al.: Chem. Ber., 101, 3659 (1968)].

Chemical synthesis of a 4-hydroxyproline-containing peptide by a combination of the Fmoc method and the active ester method requires either an active ester derivative of 4-hydroxyproline with its amino group protected by an Fmoc group, or an active ester derivative of 4-hyaroxyproline with its amino group protected by an Fmoc group and with its hydroxyl group protected. Such an active ester derivative, however, is not known.

SUMMARY OF THE INVENTION

The present invention provides 4-hydroxyproline derivatives with its amino group protected by an Fmoc group. The invention also provides 4-hydroxyproline derivatives with both its amino group protected by an Fmoc group, as well as its hydroxyl group protected by a tert-butyl group. These derivatives enable chemical synthesis of 4-hydroxyproline-containing peptides by combining the Fmoc method and the active ester methods. This invention also is directed to preparing 4-hydroxyproline derivatives and to purifying 4-hydroxyproline that has its amino group protected with an Fmoc group such as N-Fmoc-4-hydroxyproline.

The present invention therefore provides:

A process for purification of N-9-fluorenylmethoxycarbonyl)-4-hydroxyproline contained as a target compound in a liquid medium. The liquid medium that contains the target compound is treated with anhydrous magnesium sulfate to adsorb the target compound on the anhydrous magnesium sulfate, and then separating the target compound from the anhydrous magnesium sulfate. Preferably, separating the target compound from he anhydrous magnesium sulfate is conducted by collecting the anhydrous magnesium sulfate with the target compound adsorbed thereon by filtration, washing the same with an organic solvent, dissolving the anhydrous magnesium sulfate with an aqueous solution of hydrochloric acid to leave the target compound as an undissolved substance, and recovering the undissolved substance.

The invention also provides N-(9-fluorenylmethoxycarbonyl)-4-substituted proline derivatives of formula ( I ):

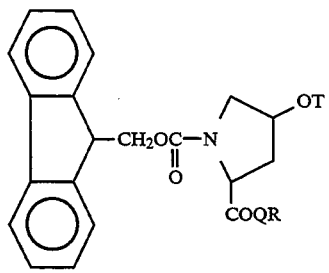

(I)

wherein
Q is an oxygen or sulfur atom; R represents a linear or branched lower alkyl, aryl, p-nitrophenyl, 1,3,5-trichlorophenyl, pentachlorophenyl, pentafluorophenyl, 2,4-dinitrophenyl, succinimidyl, phthalimidyl group, piperidinyl, 5-norbornene-2,3-dicarboxyimidyl, 8-quinolyl, 2-pyridyl, 0-hydroxyphenyl, o-(phenacyl-oxy)-phenyl, 1-benzotriazyl or 3,4-dihydro-4-oxo-1,2,3-benzotriazol-3-yl; and T represents a hydrogen atom or a tert-butyl group.

The invention still further provides N-(9-fluorenylmethoxycarbonyl)-4-hydroxy-proline derivatives of formula (II):

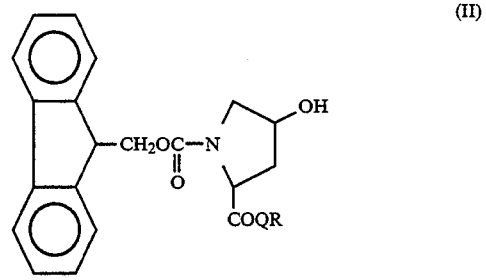

(II)

wherein
Q is an oxygen or sulfur atom; and R represents a linear or branched lower alkyl, aryl, p-nitrophenyl, 1,3,4-trichlorophenyl, pentachlorophenyl, pentafluorophenyl, 2,4-dinitrophenyl, succinimidyl, phthalimidyl group, piperidinyl, 5-norbornene-2,3-dicarboxyimidyl, 8-quinolyl, 2-pyridyl, 0-hydroxyphenyl, o-(phenacyl-oxy)-phenyl, 1-benzotriazyl or 3,4-dihydro-4-oxo-1,2,3-benzotriazol-3-yl. Preferably, Q is an oxygen atom and R is a 3,4-dihydro-4-oxo-1,2,3-benzotriazol-3-yl group. These preferred derivatives are produced by reacting 3-hydroxy-4-oxo-3,4-dihydro-1,2,3-benzotriazine with N-(9-fluorenylmethoxy-carbonyl)-4-hydroxyproline in the presence of a coupling reagent, preferably dicyclohexylcarbodiimide.

Preferred derivatives of formula (II) also include those where Q is an oxygen atom and R represents a pentafluorophenyl group. These preferred derivatives are produced by reacting pentafluorophenol with N-(9-fluorenylmethoxycarbonyl)-4-hydroxyproline in the presence of a coupling reagent, preferably dicyclohexylcarbodiimide.

N-(9-fluorenylmethoxycarbonyl)-4-tert-butyl-hydroxyproline derivative represented by formula (III) are also provided by the invention:

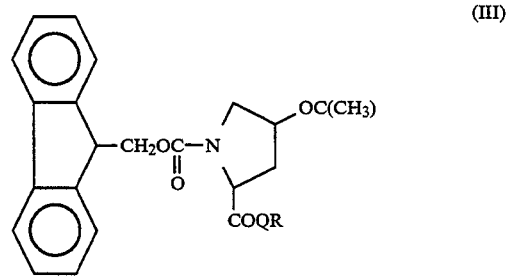

(III)

wherein
Q is an oxygen or sulfur atom; and R represents a linear or branched lower alkyl, aryl, p-nitrophenyl, 1,3,4-trichlorophenyl, pentachlorophenyl, pentafluorophenyl, 2,4-dinitrophenyl, succinimidyl, phthalimidyl group, piperidinyl, 5-norobornene-2,3-dicarboxyimidyl, 8-quinolyl, 2-pyridyl, 0-hydroxyphenyl, o-(phenacyl-oxy)-phenyl, 1-benzotriazyl or 3,4-dihydro-4-oxo-1,2,3-benzotriazol-3-yl. The compounds of formula (III) are made by reacting isobutylene with a N-(9-fluorenylmethoxycarbonyl)4-hydroxyproline derivative of formula (II) in the present of a catalytic amount of sulfuric acid. Preferably, in the compounds of formula (III) Q is an oxygen atom and R is either a pentafluorophenyl group or a 3,4-dihydro-4-oxo-1,2,3-benzotriazol-3-yl group.

A process of preparation of N-(9-fluorenylmethoxycarbonyl)4-hydroxyproline derivatives of formula (II) are also provided. The process entails reacting an electron attractive compound with N-(9-fluorenylmethoxycarbonyl)4-hydroxyproline in the presence of a coupling reagent. Preferably the coupling reagent is dicyclohexylcarbodiimide.

The preferred compounds of formula (III) where Q is oxygen and R is a pentafluorophenyl group are formed by reacting isobutylene with the N-(9-fluorenylmethoxycarbonyl)4-hydroxyproline derivative of formula (II) where Q is oxygen and R is a pentafluorophenyl group in the presence of a catalytic amount of sulfuric acid.

The invention is still further directed to preparation of the N-(9-fluorenylmethoxycarbonyl)4-tert-butyl-hydroxyproline derivatives of formula (III) where Q is oxygen and R is 3,4-dihydro-4-oxo-1,2,3-benzotriazol-3-yl, by reacting isobutylene with the N(9-fluorenylmethoxycarbonyl)4-hydroxyproline derivative of formula (II) where Q is oxygen and R is a 3,4-dihydro-4-oxo-1,2,3-benzotriazol-3-yl group in the presence of a catalytic amount of sulfuric acid.

According to the present invention, novel 4-hydroxyproline derivatives with an amino group protected by a Fmoc group, and novel 4-tert-butyl-hydroxyproline derivatives with the amino group protected by an Fmoc group are provided. These derivatives make it possible to conduct chemical synthesis of 4-hydroxyproline-containing peptide by using the Fmoc method and the active ester method in combination; a preparation process thereof; a purification process of 4-hydroxyproline with its amino group protected by an Fmoc group, i.e., N-Fmoc-4-hydroxyproline useful as one of raw materials for the derivative is also disclosed.

DETAILED DESCRIPTION OF THE INVENTION

Figure 1:
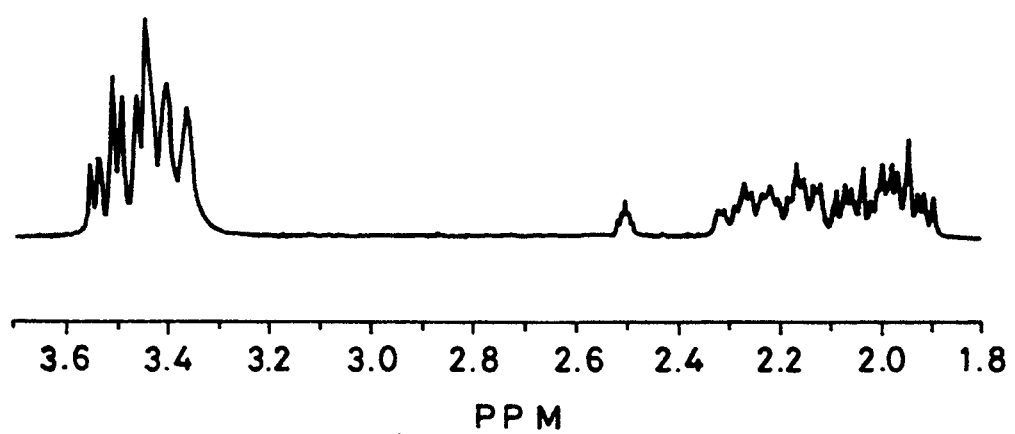
FIG. 1 is a $^1$H nuclear magnetic resonance spectrum, over a chemical shift range of 1.8–3.7 ppm, of the product A obtained in Example 1.
Figure 2:
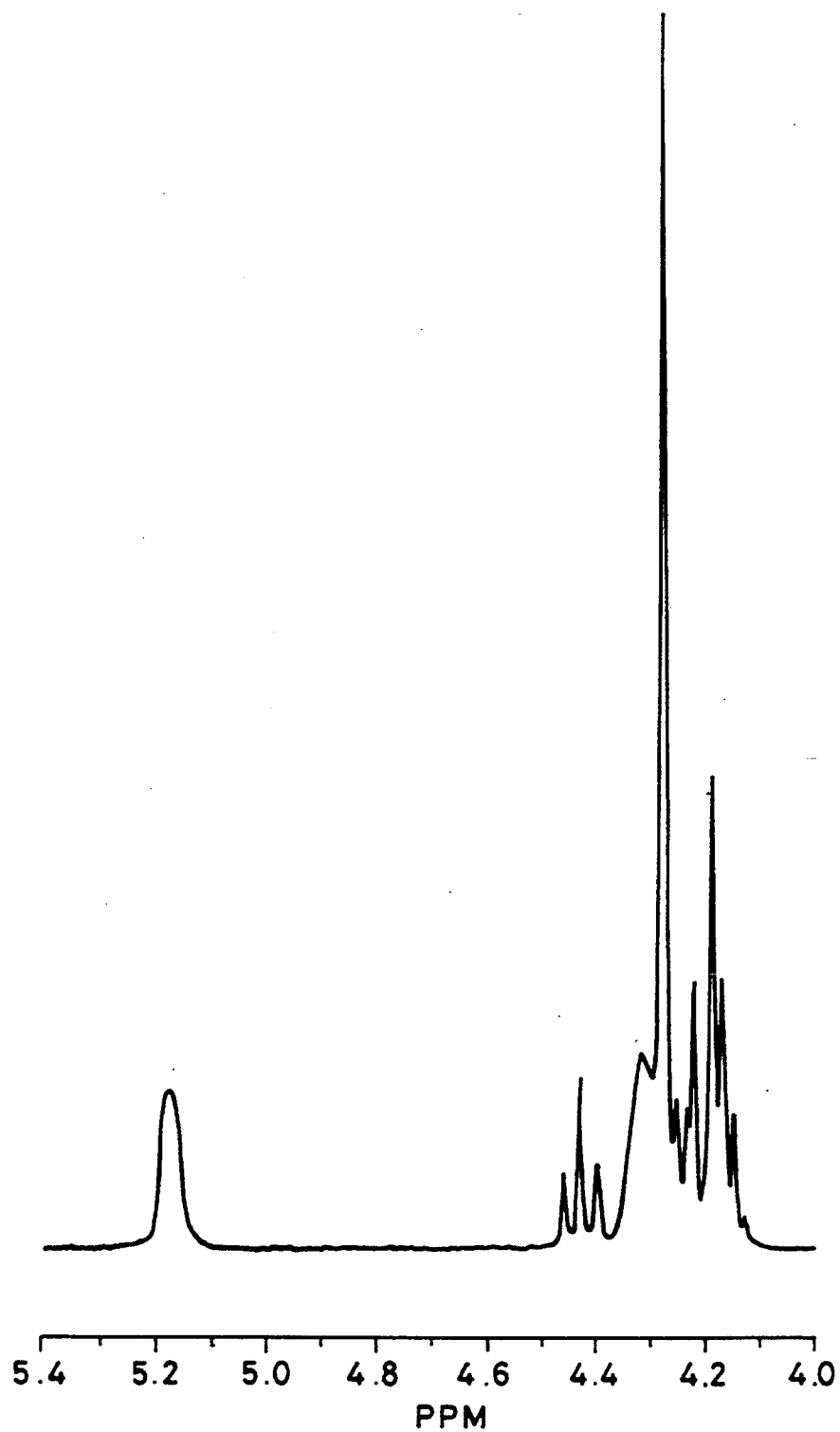
FIG. 2 is a $^1$H nuclear magnetic resonance spectrum, over a chemical shift range of 4.0–5.4 ppm, of the product A obtained in Example 1.
Figure 3:
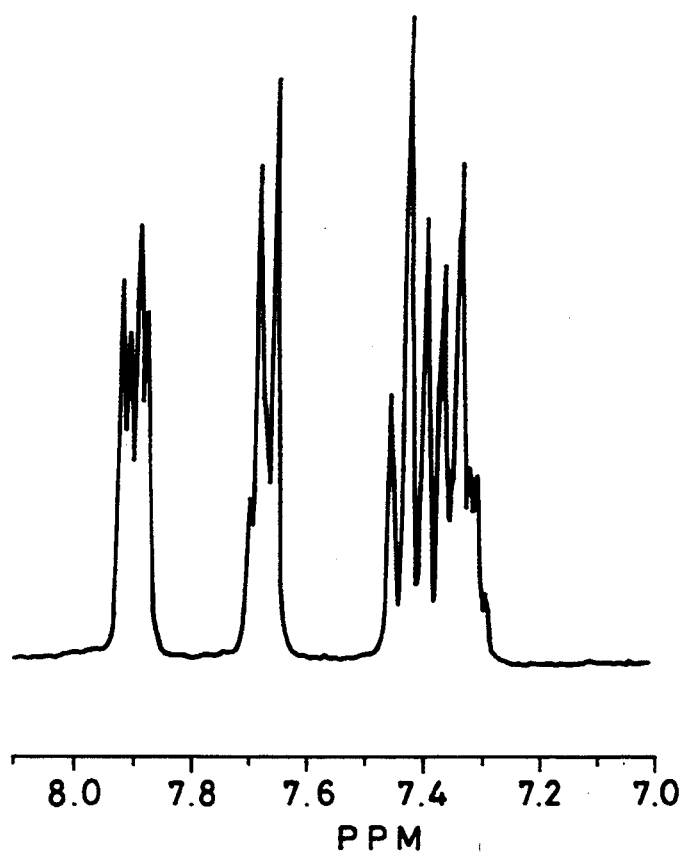
FIG. 3 is a $^1$H nuclear magnetic resonance spectrum, over a chemical shift range of 7.0–8.1 ppm, of the product A obtained in Example 1.
Figure 4:
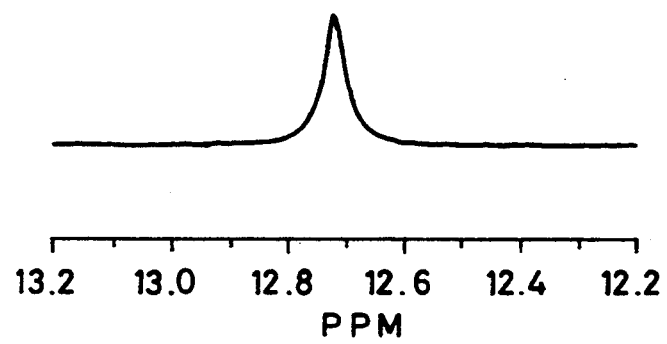
FIG. 4 is a $^1$H nuclear magnetic resonance spectrum, over a chemical shift range of 12.2–13.2 ppm, of the product A obtained in Example 1.
Figure 5:
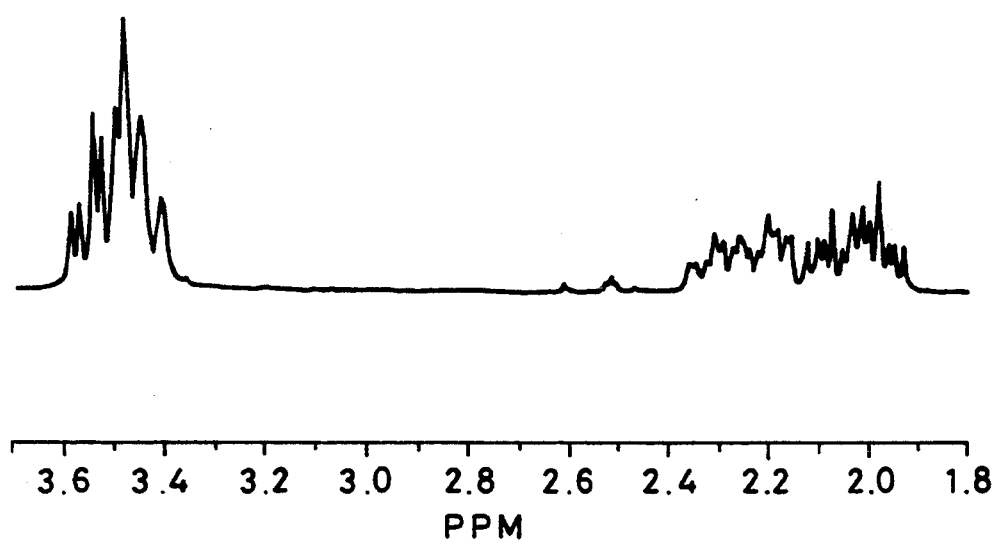
FIG. 5 is a $^1$H nuclear magnetic resonance spectrum, over a chemical shift range of 1.8–3.7 ppm, of the product B obtained in the comparison experiment in Example 1.
Figure 6:
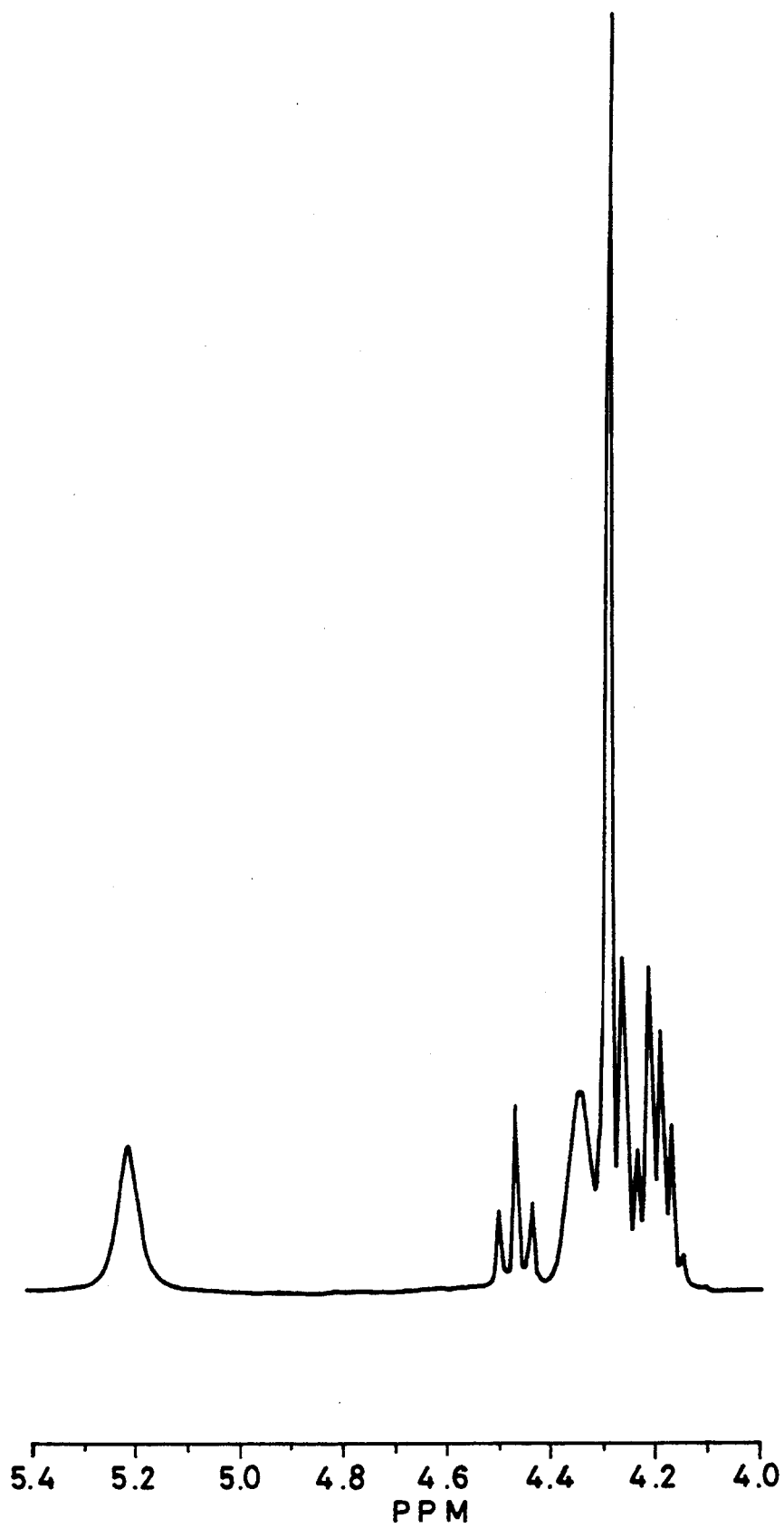
FIG. 6 is a $^1$H nuclear magnetic resonance spectrum, over a chemical shift range of 4.0–5.4 ppm, of the product B obtained in the comparison experiment in Example 1.
Figure 7:
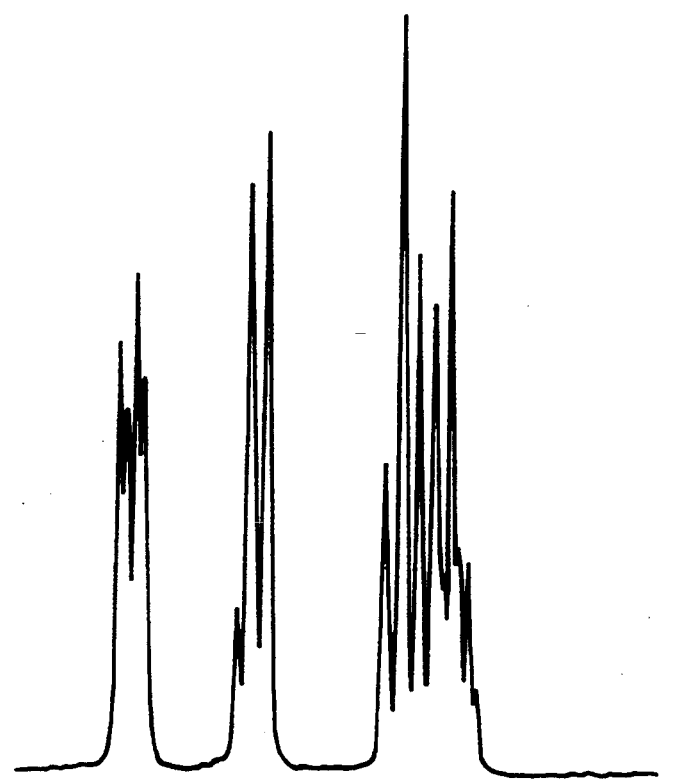
FIG. 7 is a $^1$H nuclear magnetic resonance spectrum, over a chemical shift range of 7.0–8.1 ppm, of the product B obtained in the comparison experiment in Example 1.
Figure 8:
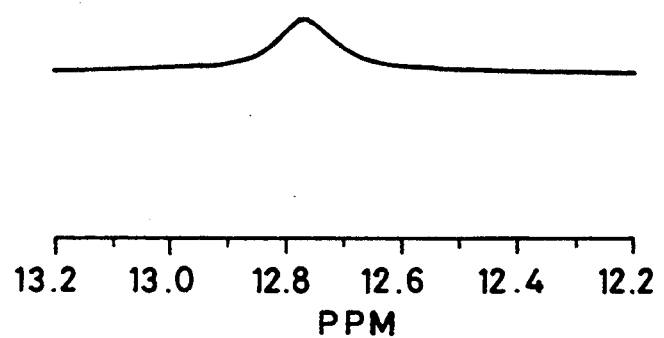
FIG. 8 is a $^1$H nuclear magnetic resonance spectrum, over a chemical shift range of 12.2–13.2 ppm, of the product B obtained in the comparison experiment in Example 1.

Although N-(9-fluorenylmethoxycarbonyl)-4-hydroxyproline (hereinafter abbreviated as "Fmoc-Hyp") useful in the present invention can be obtained by the process disclosed by L. Lapatsanis et al. [Synthesis, 671–673 (1983)] it can also be obtained by reacting an Fmoc agent, such as N-(9-fluorenylmethyl)-N-succinimidyl carbonate, with 4-hydroxyproline, the latter being in the form of a solution, while maintaining the pH at 8–12 with ammonia or an amine, followed by extraction from the reaction mixture with an organic solvent, pH adjustment, recrystallization or the like.

Fmoc-Hyp obtained in a manner as described above, however, contains impurities. It is, therefore, preferable to employ it after treating a solution of the compound with anhydrous magnesium sulfate to adsorb the solution onto the anhydrous magnesium sulfate and then collecting the Fmoc-Hyp from the anhydrous magnesium sulfate.

Crystallization-water-free anhydrous magnesium sulfate, which is usable in the present invention, is readily available on the market. An anhydrous magnesium sulfate should be used in an amount sufficient not only to adsorb water contained in the reaction mixture and also to adsorb Fmoc-Hyp.

The treatment temperature and time for adsorption of Fmoc-Hyp on anhydrous magnesium sulfate can be readily selected to assure optimum conditions depending on the amount of the anhydrous magnesium sulfate employed, the water content of the reaction mixture and the like. In general, the temperature can be a range of 0°–35° C., while the treatment time can be in a range of 1–24 hours.

The collection of Fmoc-Hyp from (anhydrous) magnesium sulfate with the Fmoc-Hyp adsorbed thereon can be conducted in the following manner. Namely, (anhydrous) magnesium sulfate with the Fmoc-Hyp target compound adsorbed thereon is collected by filtration or the like, and washed with a suitable organic solvent such as ethyl ether. The magnesium sulfate then is dissolved with an aqueous HCl solution of about pH 2. The Fmoc-Hyp is not dissolved by this operation. Insoluble materials are collected, dried by reduced-pressure drying or a like method, whereby Fmoc-Hyp is obtained in purified form.

The N-(9-fluorenylmethoxycarbonyl)-4-hydroxyproline derivatives of formula (II) can be obtained by adding an electron attractive compound to a solution of Fmoc-Hyp in an solvent in the present of a coupling reagent and then reacting them at −30° C. to 0° C. for 1–24 hours under stirring.

Examples of the solvent used in the above reaction include tetrahydrofuran, methylene chloride, carbon tetrachloride, benzene, acetonitrile, ethyl acetate, diethyl ether, dioxane, or mixtures thereof.

Illustrative coupling reagents usable in the above reaction include dicyclohexycarbodiimide, 1-ethyl-3-(3-dimethylaminopropyl) carbodiimide and N,N′-diisopropylcarbodiimide.

Exemplary electron attractive compounds include p-nitrophenol, thiophenol, p-nitrothiophenol, 1,3,5-trichlorophenol, pentachlorophenol, pentafluorophenol, 2,4-dinitrophenol, N-hydroxysuccinimide, N-hydroxyphthalimide, N-hydroxypiperdine, N-hydroxy-5-norbornene-2, 3-dicarboxyimide, 8-hydroxyquinoline, 8-hydroxy-5-chloroquinoline, 2-hydroxypyrizine, catechol, 1-hydroxybenzotriazole, o-benzylcatechol, o-phenacyl-cathecol and 3-hydroxy-4-oxo-3, 4-dihydro-1,2,3-benzotriazine (Dhbt-OH).

EXAMPLE 1

Synthesis and Purification of N-(9-fluorenyl-methoxycarbonyl)-4-L-hydroxyproline To 3.93 g (30 mmol) of trans-4-L-hydroxyproline (product of Aldrich Chemical Co. Inc.), 100 ml of distilled water is added to have the former dissolved in the latter, followed by addition of a solution of 9-fluorenyl-methyl-N-succinimidylcarbonate (11.17 g, 33 mmol, product of Cambridge Research Biochemicals, Inc.) in acetonitrile (150 ml). While being cooled over ice-water bath, to the resulting mixture is added gradually 15 ml of triethylamine (product of Kanto Chemical Co., Ltd.), followed by stirring for 30 minutes. The resulting mixture is stirred at room temperature for three hours. To the reaction mixture is added 100 ml of distilled water and 15.3 g of sodium chloride, followed by washing with 50-ml portions of diethyl ether three times. The water layer thus obtained is adjusted to pH 2 or lower with concentrated hydrochloric acid. The resulting solution is shaken three times in 100 ml of diethyl ether. To the ether layer thus obtained, 30 g of anhydrous magnesium sulfate (product of Kanto Chemical Co., Inc.) is added and the mixture is allowed to stand over night at room temperature. The reaction mixture is filtered through a millicup filter paper (product of Millipore Co., Ltd.). The residue on the millicup filter paper is washed twice with 50 ml-portions of hydrochloric acid of about 1N, followed by drying under reduced pressure, whereby 6.32 g of the reaction product (hereinafter called "Product A") is obtained (yield: 60%).

For comparison, a similar process to the above except for the omission of the adsorption of the target product on anhydrous magnesium sulfate is conducted in the following manner.

To 3.93 g (30 mmol) of trans-4-hydroxy-L-proline (Aldrich Chemical Co., Inc.), 100 ml of distilled water is added to have the former dissolve in the latter. To the resulting solution is added a solution of 9-fluorenyl-methyl-N-succinimidyl carbonate (10.12 g, 30 mmol; product of Cambridge Research Biochemicals Inc.) in 150 ml of acetonitrile. While the resulting mixture is cooled over ice-water bath, 15 ml of triethyl amine (product of Kanto Chemical Co., Ltd.) is added gradually in portions, followed by stirring for 20 minutes. To the reaction mixture is added 150 ml of distilled water and 16 g of sodium chloride, followed by washing with 50-ml-portions of diethyl ether three times. The water layer is adjusted to pH 2 or lower with concentrated hydrochloric acid. The resulting solution is shaken three times in 50 ml of diethyl ether. The ether layer is separated, and 3 g of anhydrous magnesium sulfate (product of Kanto Chemical Co, Ltd.) is added for drying. After the mixture is allowed to stand at room temperature over night, the magnesium sulfate is removed by filtration. The filtrate is concentrated to about 5 ml in a rotary evaporator and then allowed to crystallize, whereby 6.52 g of a reaction product (hereinafter called "Product B") is obtained (yield: 61%).

Figure 9:
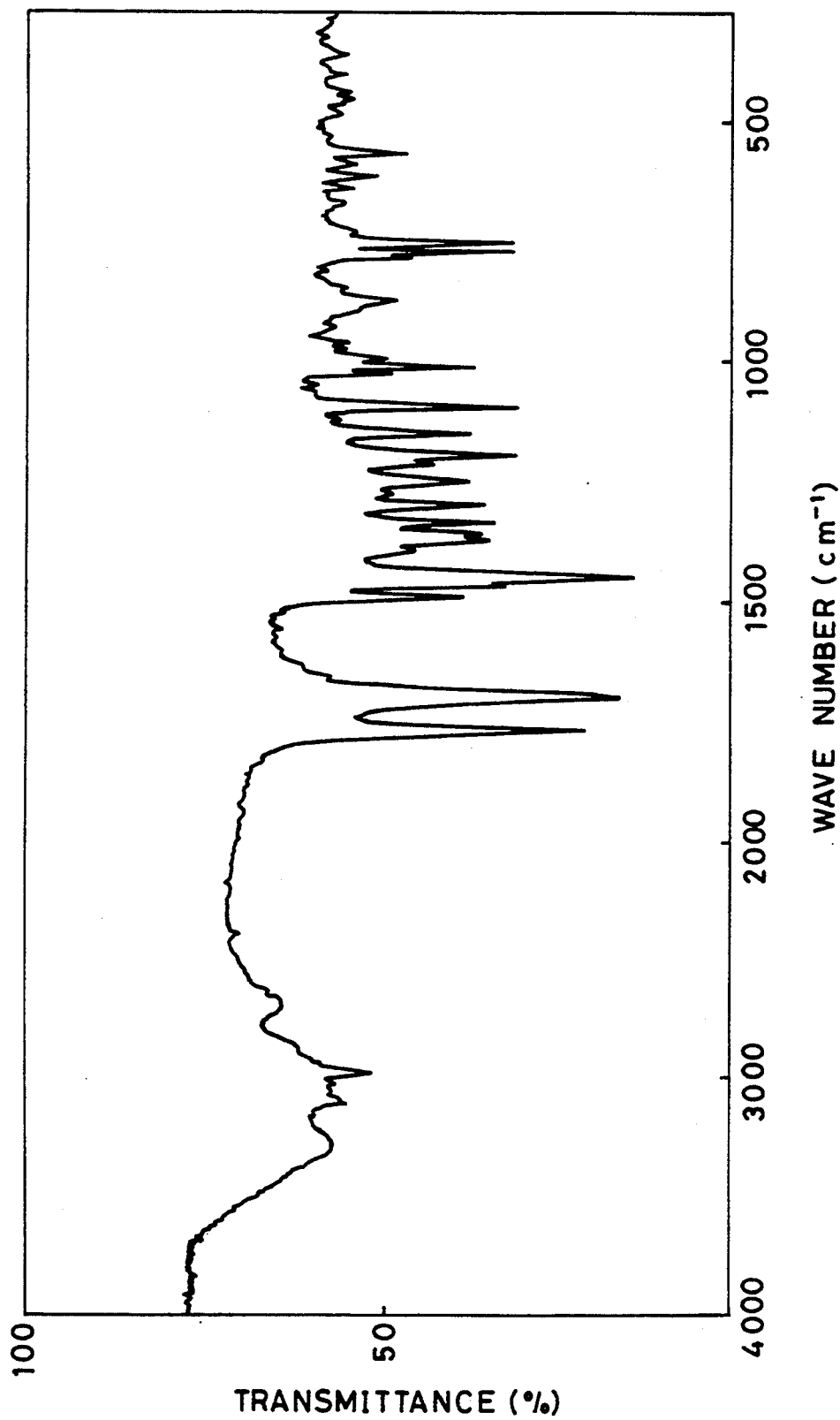
FIG. 9 is an infrared ray absorption spectrum of the product A obtained in Example 1.
Figure 10:
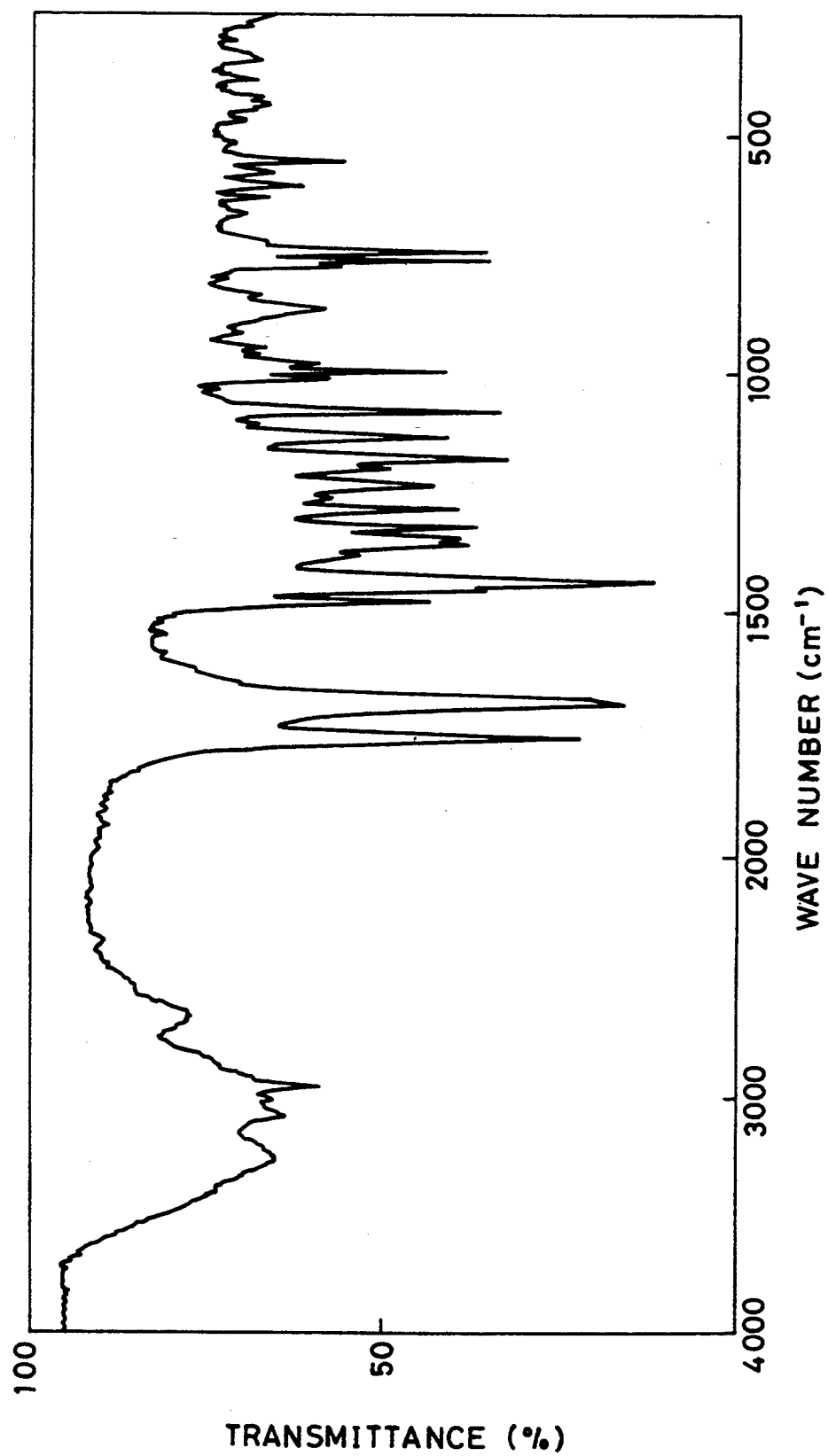
FIG. 10 is an infrared ray absorption spectrum of the product B obtained in the comparison experiment in Example 1.

In FIGS. 1–4 (FIGS. 5–8 for Product B obtained in the comparison test), $^1$H nuclear magnetic resonance spectra of product A purified by the method described above, are shown only over the ranges with absorption. Infrared ray spectrum of Product A is shown in FIG. 9 (FIG. 10 for Product B obtained in the comparison test), while the results of high-performance liquid chromatography are shown in Tables 1 and 2. These results show that Product A obtained by the purification process according to the present invention is N-(9-fluorenylmethoxycarbonyl)-4-L-hydroxyproline, like Product B.

Incidentally, each $^1$H nuclear magnetic resonance spectrum of product A and product B is measured by a nuclear magnetic resonance apparatus ("AC-250 Model" trade name, manufactured by Bulquor Co., Ltd.). As regards to the high-performance liquid chromatography (main unit: "600 series", trade name; manufactured by Waters Corp.), columns 3.9 mm×15 cm is packed with "μBondasphere 5μc18-100A" (trade name; manufactured by Waters corp.) are used. A 50:50 mixture of water and acetonitrile is used as a developer. The flow rate is set at 1.0 ml/min and the detection is carried out at the wavelength of 254 nm. Each infrared ray absorption spectrum is measured by the KBr tablet method, using an infrared analyzer ("270-50 Model", trade name; manufactured by Hitachi Ltd.).

TABLE 1

Results of High-Performance Liquid Chromatography of the Reaction Products Obtained in Example 1

| Sample | Retention time (min) | Purity (%) |
| --- | --- | --- |
| Product A | 1.79 | 99.6 |
| Product B | 1.80 | 99.6 |

TABLE 2

Elemental Analysis Data of the Reaction Products Obtained in Example 1

| Sample | Carbon | Hydrogen | Nitrogen |
|---|---|---|---|
| Product A | 67.91 | 5.44 | 3.86 |
| Product B | 67.92 | 5.47 | 3.91 |
| Calculated | 68.0 | 5.4 | 4.0 |

EXAMPLE 2

Synthesis of the 3-hydroxy-4-oxo-3,4-dihydro-1,2,3-benzotriazine ester of N-(9-fluorenyl-methoxycarbonyl) 4-L-hydroxyproline (Fmoc-Hyp-ODhbt)

Dissolved in 10 ml of tetrahydrofuran are 245 mg (1.5 mmol) of 3-hydroxy-4-oxo-3,4-dihydro-1,2,3-benzotriazine and 310 mg (1.5 mmol) of dicyclohexylcarbodiimide. The vessel is purged with argon gas. While the vessel is cooled at −15° C., the contents are allowed to stand for 5 minutes. The vessel is charged with a solution of Product A obtained in Example 1, that is, N-(9-fluorenylmethoxycarbonyl)-4-L-hydroxy-proline (530 mg, 1.5 mmol) in 10 ml of tetrahydrofuran and is sealed hermetically. The resultant mixture is stirred for one hour, followed by an additional two-hour stirring under ice cooling. It is observed that with the progress of the reaction, the reaction mixture changed from yellow to white and dicyclohexylurea precipitated. After the reaction mixture is concentrated and the solvent is purged with ethyl acetate, dicyclohexylurea is removed by filtration. The filtrate is concentrated to about 5 ml, followed by the addition of n-hexane, whereby a pale yellow precipitate is obtained. After the resulting mixture is allowed to stand overnight, the precipitate is collected by filtration and dried in a desiccator. The dried substance is dissolved again in ethyl acetate, to which n-hexane is added for precipitation, so that 685 mg of the product is obtained.

As a result of an analysis by thin-layer chromatography (developer: ethyl acetate) on a silica gel plate ("Kieselguhr 60F$_{254}$" product of Merck & Company, Inc.), the product is found to contain a byproduct (Rf=0.20) in addition to the target product (Rf=0.75). Accordingly, the reaction product is dissolved in ethyl acetate, loaded on a column (15 mm inner diameter×400 mm length) packed with silica gel ("Kieselguhr 60" product of Merck & Company, Inc.) as a carrier, and the column is rapidly eluted by flash chromatography while using ethyl acetate as a developer. After it is confirmed by thin-layer chromatography on a silica gel plate that the eluate contained only one component (Rf=0.75), the eluate is concentrated under reduced pressure to distill off ethyl acetate. To the residue thus obtained is added n-hexane, whereby 479 mg of a precipitate (purified product) is obtained (yield: 64%).

The following are the analysis data of the precipitate (purified product) obtained.

Figure 11:
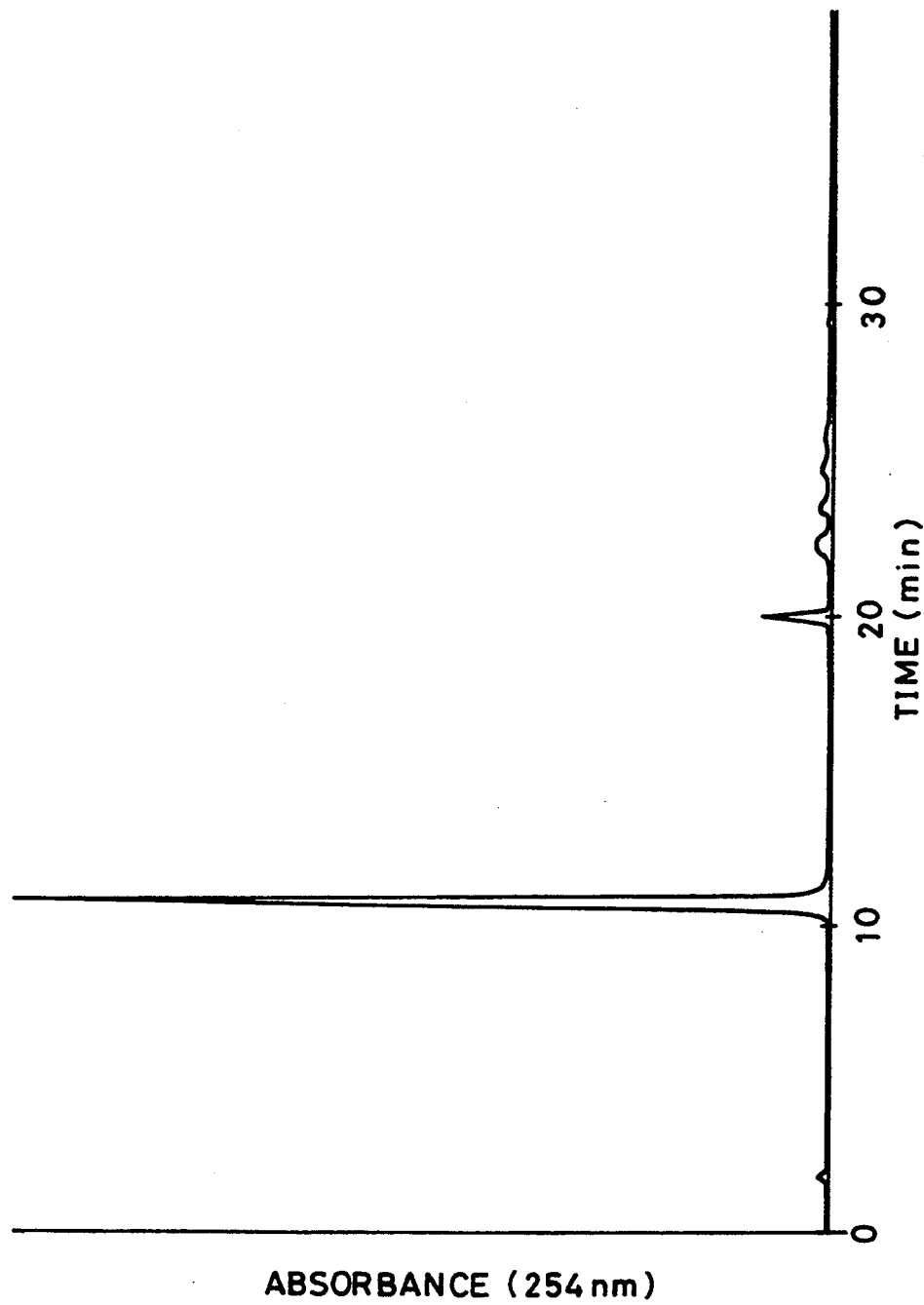
FIG. 11 is a high-performance liquid chromatogram of the 3-hydroxy-4-oxo-3,4-dihydro-1,2,3-benzotriazine ester of N-(9-fluorenylmethoxycarbonyl)-4-hydroxyproline according to the present invention.
Figure 12:
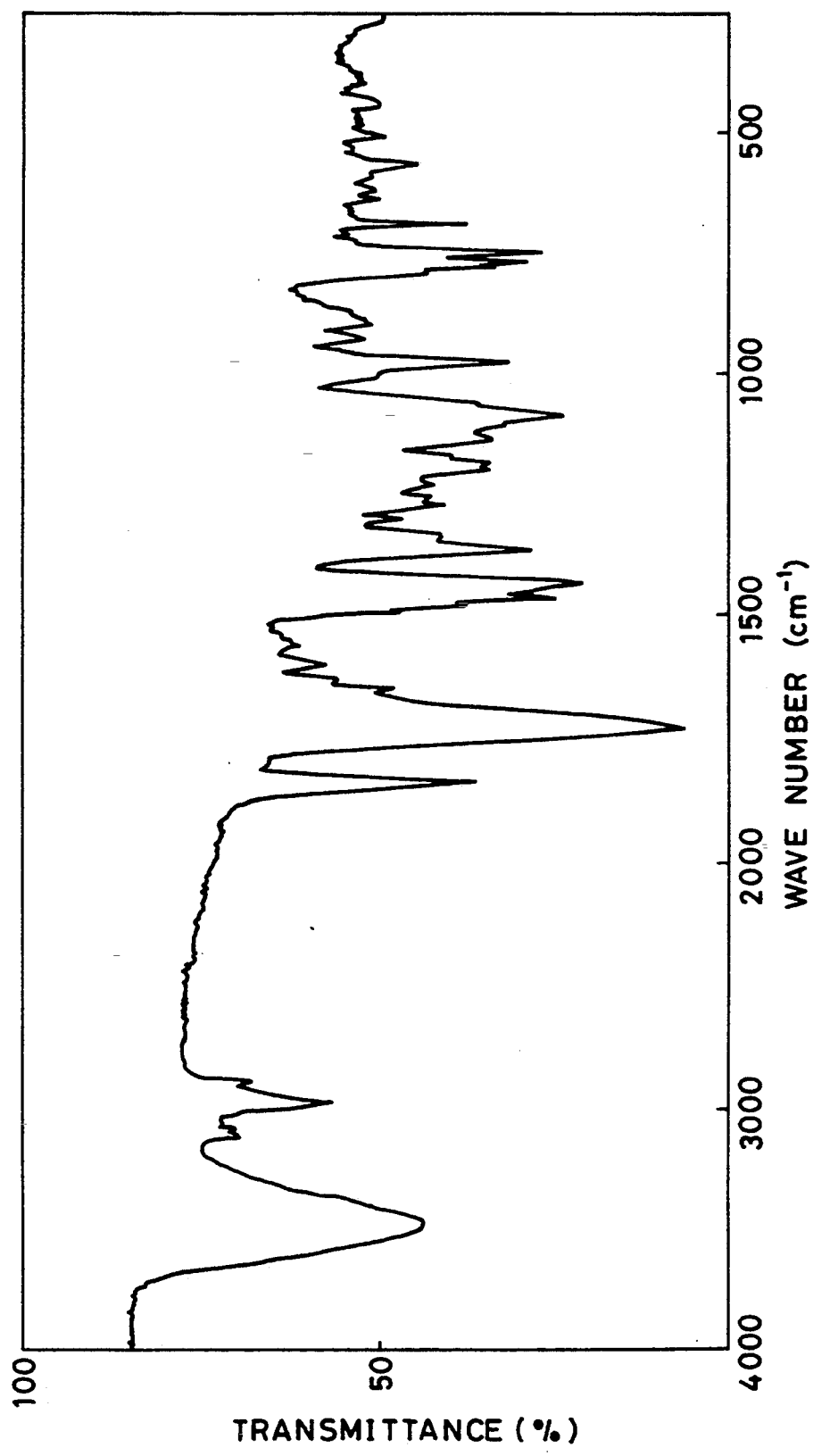
FIG. 12 is an infrared ray absorption spectrum of the 3-hydroxy-4-oxo-3,4-dihydro-1,2,3-benzotriazine ester of N-(9-fluorenylmethoxycarbonyl)-4-hydroxyproline according to the present invention.
Figure 13:
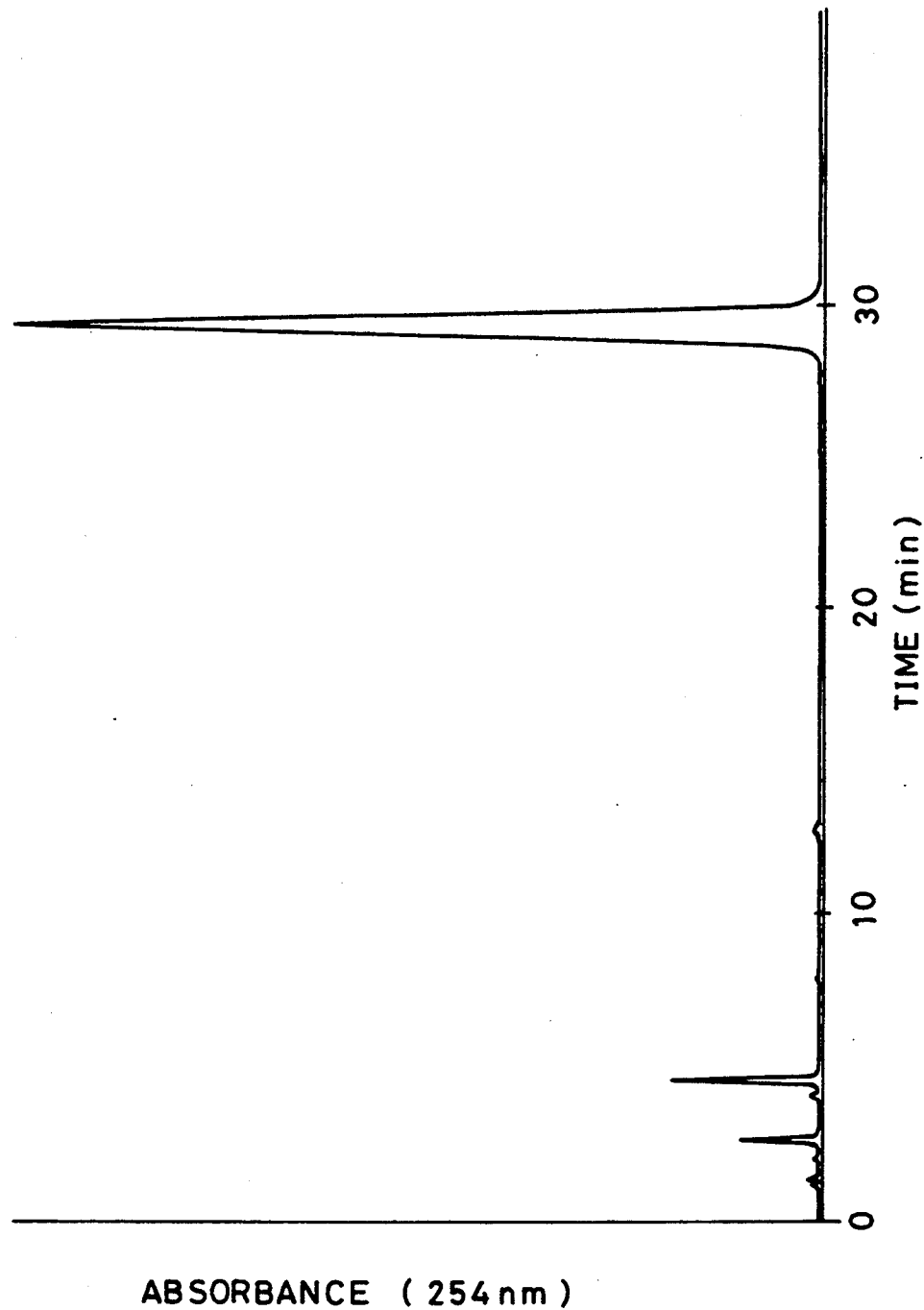
FIG. 13 is a high performance liquid chromatogram of the pentafluorophenyl ester of N-(9-fluorenylmethoxycarbonyl)-4-hydroxyproline according to the present invention.

High-performance liquid chromatography: FIG. 11
Infrared ray absorption spectrum (KBr table method): FIG. 12
$^1$H Nuclear magnetic resonance spectrum (250 MHz, DMSO-d$_6$, ppm):
δ8.4–δ8.3 (m, 2H),
δ8.2–δ8.1 (m, 1H),
δ8.1–δ8.0 (m, 1H),
δ8.0–δ7.9 (m, 2H),
δ7.7–δ7.6 (m, 2H),
δ7.5–δ7.3 (m, 4H),
δ5.4 (s, 1HO,
δ5.1–δ4.8 (m, 1H),
δ4.5–δ4.2 (m, 4H),
δ3.7–δ3.5 (m, 2H),
δ2.5–δ2.4 (brd, 2H).

According to the above results, the precipitate (purified product) has been confirmed to be the compound represented by the formula (V):

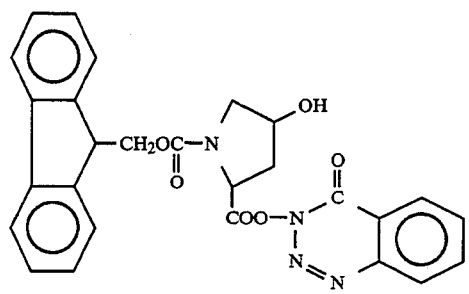

EXAMPLE 3

Synthesis of the pentafluorophenyl ester of N-(9-fluorenylmethoxycarbonyl)-4-L-hydroxyproline (Fmoc-Hyp-OPfp)

Suspended in 200 ml of acetonitrile are N-(9-fluorenylmethoxycarbonyl)-4-L-hydroxyproline (20.5 g, 50 mmol), followed by the addition of 12 ml of N, N'-dimethylformamide under ice cooling. The resulting mixture is stirred, to which 11.9 g (1.1 equivalents) of pentafluorophenol and 13.2 g (1.1 equivalents) of dicyclohexylcarbodiimide are added. The resulting suspension is stirred for one hour and then, stirred overnight at room temperature. Dicyclohexylurea produced by the reaction is removed by filtration and the filtrate is concentrated. The concentrate is dissolved in ethyl acetate. Dicyclohexylurea, which remained undissolved, is removed by filtration. The operations of dissolution in ethyl acetate, filtration, and concentration are additionally repeated twice. N,N'-Dimethylformamide contained in the concentrate is completely distilled off under reduced pressure. The concentrate is dissolved in ethyl acetate, and to the resulting solution is added n-hexane for re-precipitation, whereby 28.0 g of the product is obtained (yield: 93%).

The following are the analytical data of the product thus obtained.

Figure 14:
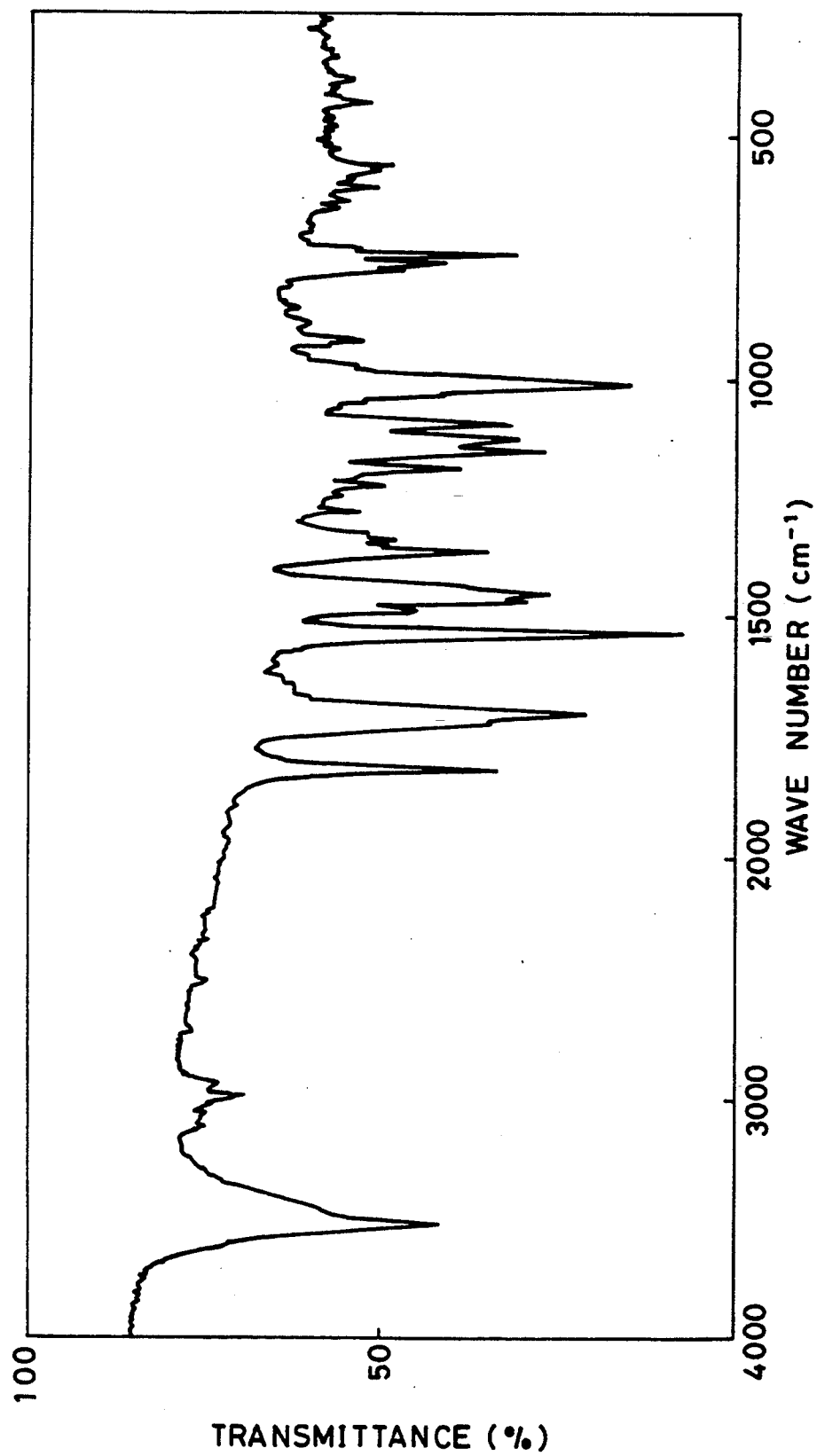
FIG. 14 is an infrared ray absorption spectrum of the pentafluorophenyl ester of N-(9-fluorenylmethoxycarbonyl)-4-hydroxyproline according to the present invention.

Infrared ray absorption spectrum (KBr tablet method): FIG. 14
$^1$H Nuclear magnetic resonance spectrum (250 Mhz, CDCl$_3$, ppm):
δ7.8–δ7.7 (m, 2H),
δ7.6–δ7.5 (m, 2H),
δ7.4–δ7.2 (m, 4H),
δ4.9–δ4.8 (m, 1H),
δ4.6 (s, 1H),
δ4.5–δ4.3 (m, 4H),
δ3.8–δ3.6 (m, 2H),
δ2.6–δ2.3 (m, 2H).

According to the above results, 1 the precipitate (purified product) has been confirmed to be the compound represented by the formula (VI):

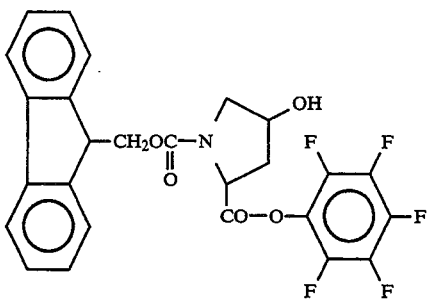

(VI)

EXAMPLE 4

Synthesis of the 3,4-dihydro-4-oxo-1,2,3,-benzotriazine-3-yl ester of N-(9-fluorenylmethoxycarbonyl)-4-tert-butyl-hydroxyproline [Fmoc-Hyp (t-Bu)-ODthb]

The 3,4-dihydro-4-oxo-1,2,3-benzotriazine-3-yl ester of N-(9-fluorenylmethoxycarbonyl)-4-L-hydroxyproline (8.1 g, 16.2 mmol) is charged into a vessel and then dissolved in 40 ml of methylene chloride. While being cooled by dry ice-methanol, to the solution is added 18.2 g (20 equivalents) of isobutylene and 0.2 ml of concentrated sulfuric acid. After the vessel is sealed hermetically and the temperature is raised to room temperature, the resulting mixture is stirred for 2 days. After removal of isobutylene and methylene chloride under reduced pressure, to the reaction mixture is added 70 ml of an aqueous solution of sodium chloride, and 100 ml of ethyl ether, and then shaken, whereby the ether layer is collected. Further, this ether extraction is repeated twice (70 ml, 50 ml). The ether extracts are combined and dried over anhydrous magnesium sulfate. After ether is distilled off under reduced pressure, the residue is dried in a desiccator under reduced pressure, whereby 8.3 g of the product are obtained in the form of amorphous solid. The product is subjected to thin-layer chromatography (developer: diethyl ether) on a silica gel plate ("Kieselguhr 60F$_{254}$", trade name; product of Merck & Company, Inc.), resulting in the detection of spots of the unreacted substances as well as that of the target product (Rf=0.79). Accordingly, the product is adsorbed on a column (30 mm in inner diameter×300 mm in length) packed with a carrier "Silica Gel 60" (trade name, product of Merck & Company, Inc.) and then eluted by flash chromatography with diethyl ether as a solvent. After it is confirmed by thin-layer chromatography on the silica gel plate that the eluate contains only one component, ether is distilled off under reduced pressure and the residue is dried in a desiccator under reduced pressure, whereby 6.72 g of the purified product are obtained in the form of an amorphous solid (yield: 74.9%).

Figure 15:
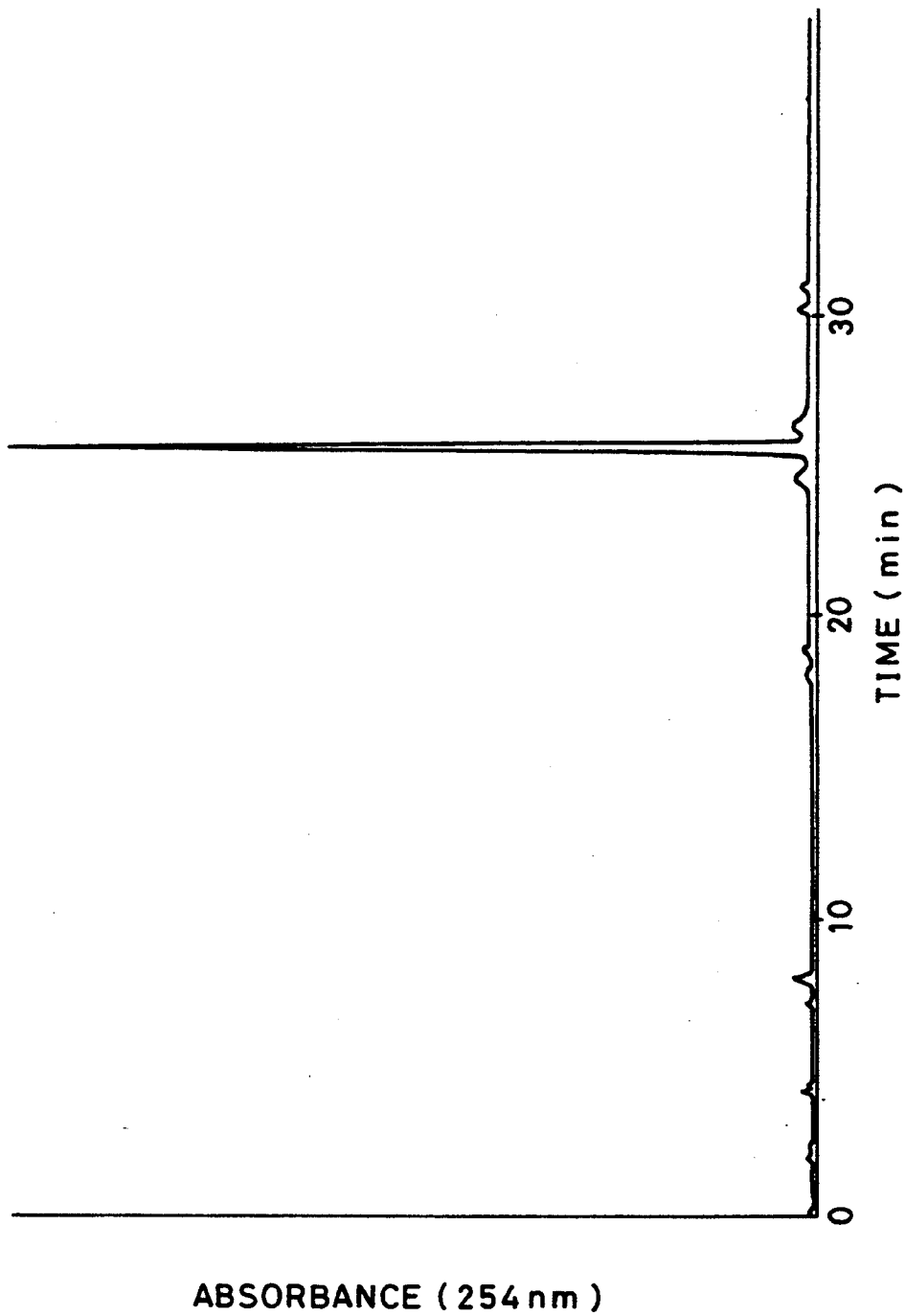
FIG. 15 is a high-performance liquid chromatogram of the 3,4-benzotriazine-3-yl ester of N-(9-fluorenylmethoxycarbonyl)-4-tert-butyl-hydroxyproline according to the present invention.
Figure 16:
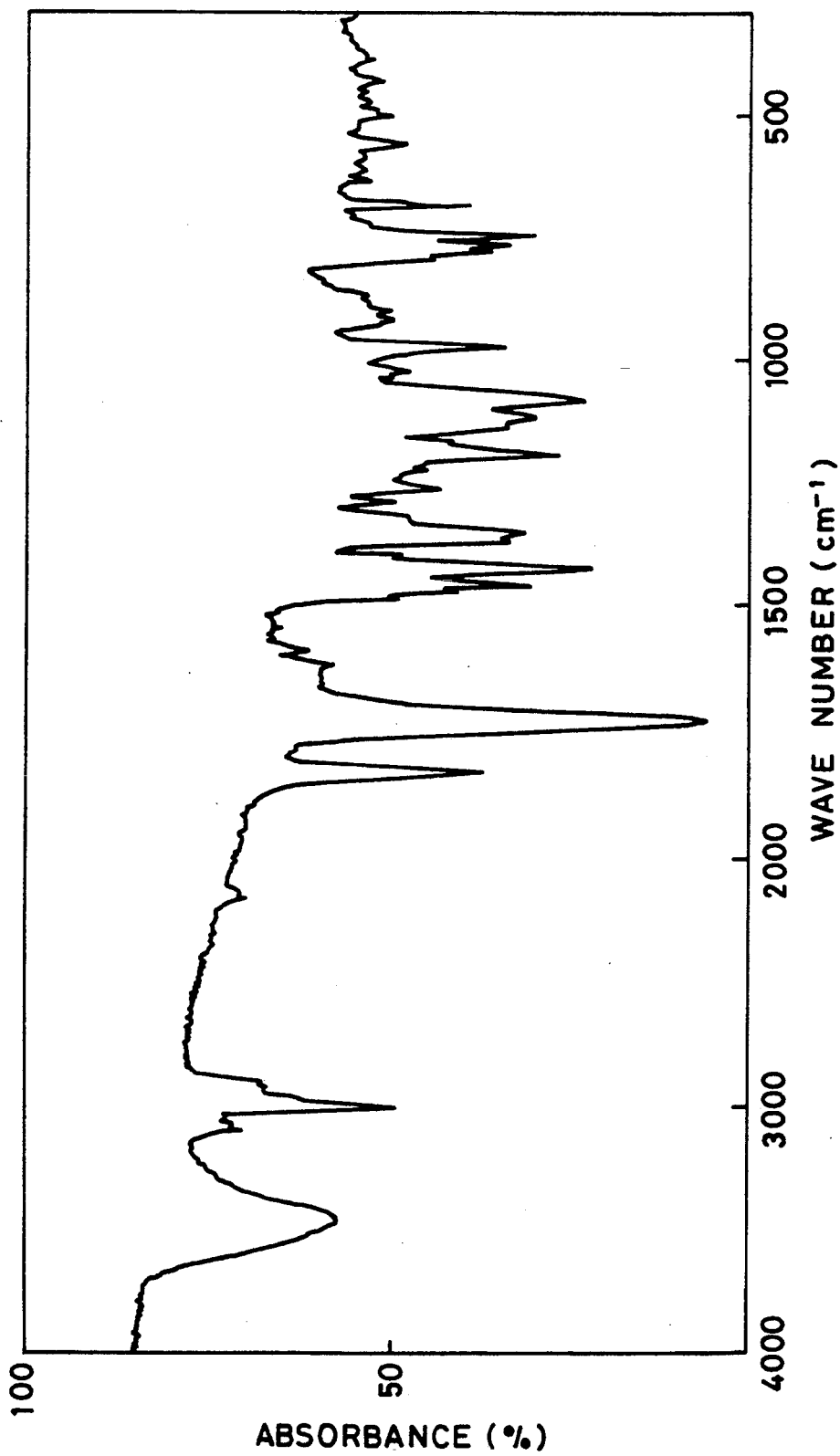
FIG. 16 is an infrared ray spectrum of the 3,4-dihydro-4-oxo-1,2,3-benzotriazine-3-yl ester of N-(9-fluorenylmethoxycarbonyl)-4-tert-butyl-hydroxyproline according to the present invention.

The following are the analysis data of the purified product thus obtained:

High-performance liquid chromatography: FIG. 15
Infrared ray absorption spectrum (KBr tablet method): FIG. 16
$^1$H Nuclear magnetic resonance spectrum (250 MHz, DMSO-d$_6$, ppm):
δ8.4–δ8.3 (m, 2H),
δ8.2–δ8.1 (m, 1H),
δ8.2–δ8.1 (m, 1H),
δ8.0–δ7.9 (m, 2H),
δ7.7–δ7.6 (m, 2H),
δ7.5–δ7.3 (m, 4H),
δ5.1–δ4.8 (m, 1H),
δ4.5–δ4.2 (m, 4H),
δ3.7–δ3.2 (m, 2H),
δ2.5–δ2.4 (m, 2H),
δ1.2 (d, 9H).

Angle of rotation [α] (25° C., DMF, c=0.440 g/dl, L=10.0 cm): −104.72

According to the above results, the purified product has been confirmed to be the 3,4-dihydro-4-oxo-1,2,3-benzotriazine-3-yl ester of N-(9-fluorenylmethoxycarbonyl)-4-tert-butyl-hydroxyproline represented by the following formula (VII):

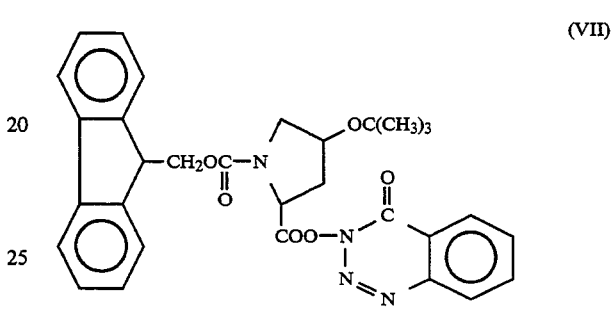

(VII)

EXAMPLE 5

Synthesis of the pentafluorophenyl ester of N-(9-fluorenylmethoxycarbonyl)-4-tert-butyl-hydroxyproline [Fmoc-Hyp(t-Bu)-OPfp]

Methoxycarbonyl-4-L-hydroxyproline (22.36 g, 43 mmol) is charged in a vessel and then dissolved in 60 ml of methylene chloride. While being cooled by a dry ice-methanol, to the solution is added 18.2 g (20 equivalents) of isobutylene and 0.2 ml of concentrated sulfuric acid. After the vessel is sealed hermetically, the resulting solution is stirred at room temperature for 2 days. After removal of isobutylene and methylene chloride under reduced pressure, to the reaction mixture is added 70 ml of an aqueous solution of sodium chloride and 100 ml of ethyl ether and then shaken, whereby the ether layer is collected. This ether extraction is repeated twice (70 ml, 50 ml). The ether extracts are combined and dried over anhydrous magnesium sulfate. After ether is distilled off under reduced pressure, the residue is dried in a desiccator under reduced pressure, whereby 18.94 g of oily product is obtained. The product is subjected to thin-layer chromatography (developer: 4:1 mixed solvent of n-hexane and ethyl acetate, by volume ratio) on a silica gel plate ("Kieselguhr 60F$_{254}$", trade name; product of Merck & Company, Inc.), resulting in the detection of spots of the unreacted substance and the byproduct, as well as that of the target product of Rf=0.50. Accordingly, the reaction product is subjected to thin-layer chromatography on a silica gel plate ("F$_{254}$S" trade name; product of Merck & Company, Inc., 20 cm×20 cm) for separation and the target product is extracted from the thin-layer with diethyl ether. The extract is concentrated to distill off ether and then the residue is dried in a desiccator under reduced pressure, whereby purified product is obtained in the form of an amorphous solid.

Figure 17:
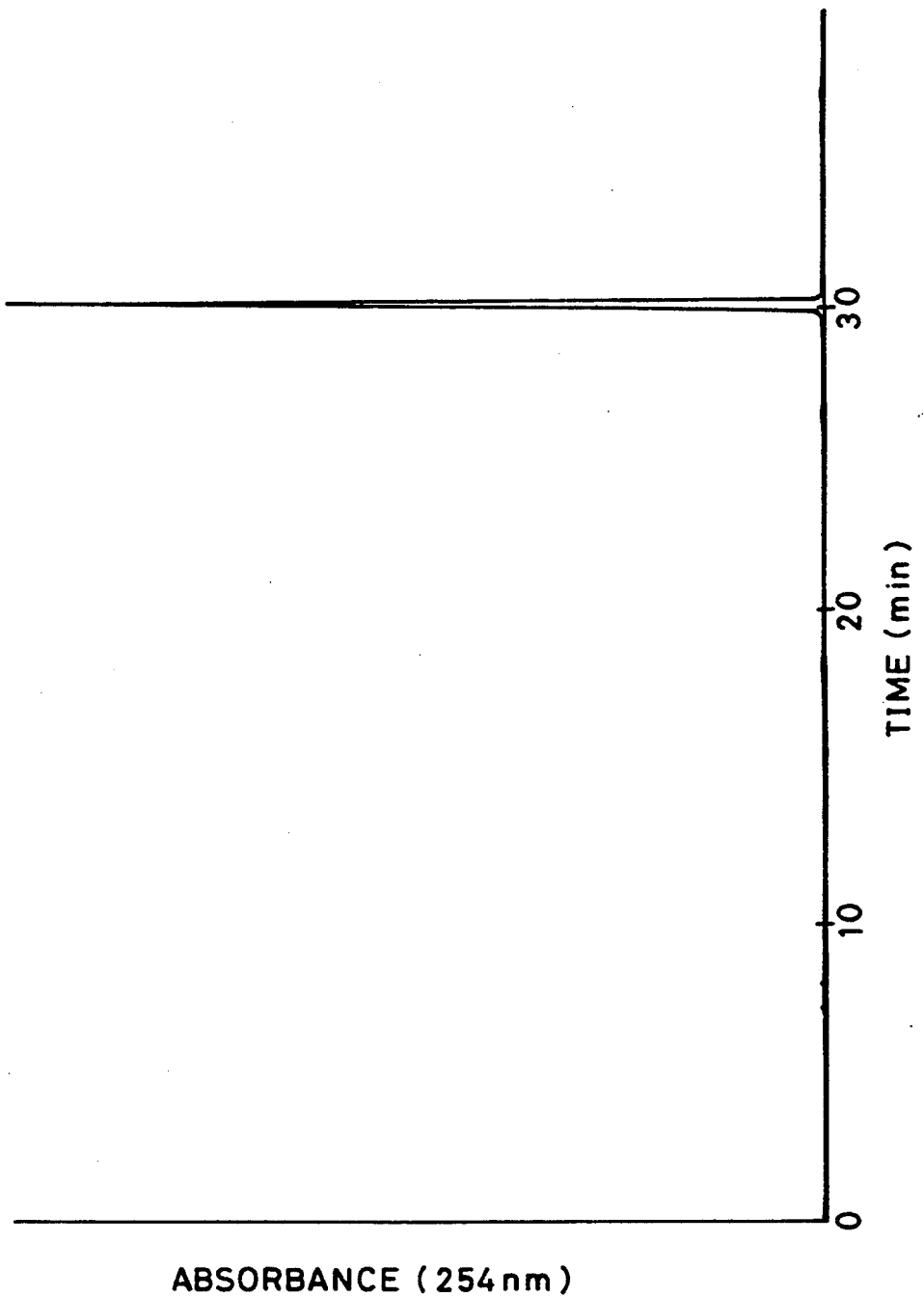
FIG. 17 is a high performance liquid chromatogram of the pentafluorophenyl ester of N-(9-fluorenylmethoxycarbonyl)-4-tert-butyl-hydroxyproline according to the present invention.

The following are the analysis data of purified product thus obtained:

High-performance liquid chromatography: FIG. 17

Figure 18:
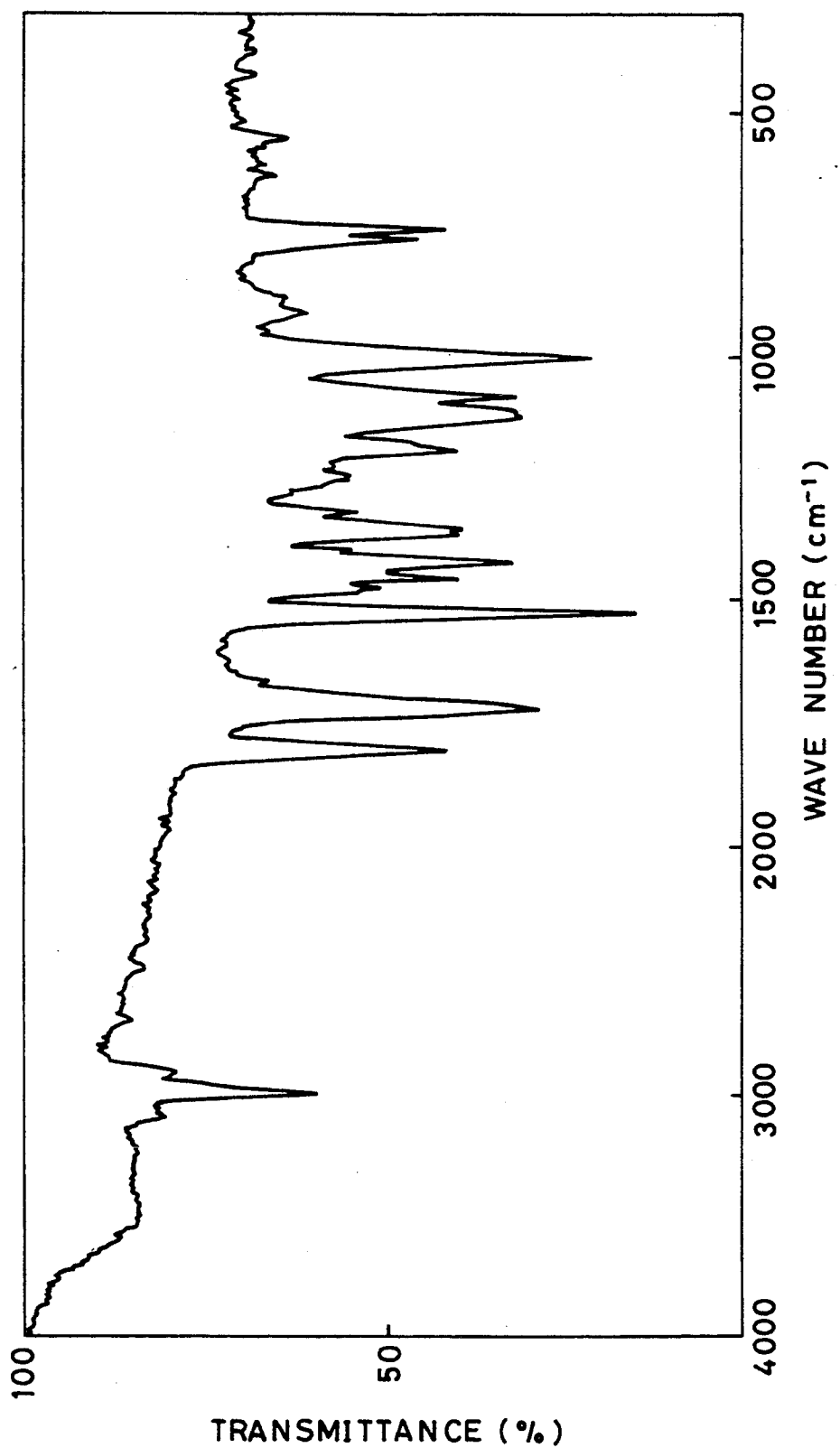
FIG. 18 is an infrared ray absorption spectrum of the pentafluorophenyl ester of N-(9-fluorenylmethoxycarbonyl)-4-tert-butyl-hydroxyproline according to the present invention.

Infrared ray absorption spectrum (neat, KRS): FIG. 18

$^1$H Nuclear magnetic resonance spectrum (250 MHz, CDCl$_3$, ppm):

δ7.8–δ7.7 (m, 2H),

δ7.6–δ7.5 (m, 2H),

δ7.4–δ7.2 (m, 4H),

δ4.9–δ4.7 (m, 1H),

δ4.5–δ4.2 (brd, 4H),

δ3.8–δ3.4 (brd, 2H),

δ2.5–δ2.3 (brd, 2H),

δ1.3–δ1.2 (brd, 9H),

Angle of rotation [α] (25° C., DMF, c=0.440 g/dl, L=10.0 cm): −27.95.

According to the above results, the purified product thus obtained has been confirmed to be the pentaluorophenyl ester of N-(9-fluorenylmethoxy-carbonyl)-4-tert-butyl-hydroxyproline represented by the following formula (VIII):

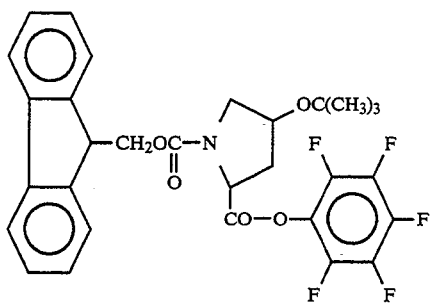

(VIII)

We claim:

1. A process for the purification of N-(9-fluorenylmethoxycarbonyl)-4-hydroxyproline contained as a target compound in a liquid medium, which comprises treating the compound-containing liquid medium with anhydrous magnesium sulfate to adsorb the target compound on the anhydrous magnesium sulfate and then collecting the target compound from the anhydrous magnesium sulfate.

2. The process of claim 1, wherein the collection of the target compound from the anhydrous magnesium sulfate is conducted by collecting the anhydrous magnesium sulfate with the target compound adsorbed thereon by filtration, washing the same with an organic solvent, dissolving the anhydrous magnesium sulfate with any aqueous solution of hydrochloric acid to leave the target compound as an undissolved substance, and then recovering the undissolved substance.

* * * * *